United States Patent [19]

Harrison et al.

[11] Patent Number: 4,806,361

[45] Date of Patent: Feb. 21, 1989

[54] MEDICAMENTS IN SUSTAINED RELEASE UNIT DOSE FORM

[75] Inventors: Paul J. Harrison; John R. Langridge; Christopher J. Potter, all of Alnwick, United Kingdom

[73] Assignee: Sterling Drug Inc., New York, N.Y.

[21] Appl. No.: 738,133

[22] Filed: May 24, 1985

[30] Foreign Application Priority Data

Jun. 4, 1984 [GB] United Kingdom ............... 84-14220

[51] Int. Cl.$^4$ .......................... A61K 9/16; A61K 9/50; A61K 31/44
[52] U.S. Cl. .................................... 424/495; 424/494; 514/334
[58] Field of Search ...................... 424/19, 28, 35, 21, 424/28, 494, 495; 514/334

[56] References Cited

U.S. PATENT DOCUMENTS

| | | | |
|---|---|---|---|
| 2,887,440 | 5/1959 | Greminger et al. | 424/19 |
| 2,921,883 | 1/1960 | Reese et al. | 424/19 |
| 3,328,256 | 6/1967 | Gaunt | 424/19 |
| 3,492,397 | 1/1970 | Peters et al. | 424/20 |
| 4,001,390 | 1/1977 | Ohno et al. | 424/35 |
| 4,138,475 | 2/1979 | McAinsh et al. | 424/19 |
| 4,180,559 | 12/1979 | Huber | 424/35 |
| 4,248,858 | 2/1981 | Guley et al. | 424/21 |
| 4,263,273 | 4/1981 | Appelgren et al. | 424/21 |
| 4,313,951 | 2/1982 | Lesher et al. | 514/334 |
| 4,361,546 | 11/1982 | Stricker et al. | 424/19 |
| 4,367,217 | 1/1983 | Gruber et al. | 424/19 |
| 4,369,172 | 1/1983 | Schor et al. | 424/19 |
| 4,385,078 | 5/1983 | Onda et al. | 424/35 |
| 4,389,393 | 6/1983 | Schor et al. | 424/19 |
| 4,415,547 | 11/1983 | Yu et al. | 424/19 |
| 4,438,091 | 3/1984 | Gruber et al. | 424/21 |
| 4,596,705 | 6/1986 | Schepky et al. | 424/35 |

FOREIGN PATENT DOCUMENTS

| | | |
|---|---|---|
| 1200494 | 2/1986 | Canada . |
| 2313915 | 1/1977 | France . |
| 2065642 | 7/1981 | United Kingdom . |
| 2151920 | 7/1985 | United Kingdom . |

*Primary Examiner*—Douglas W. Robinson
*Attorney, Agent, or Firm*—William G. Webb; Paul E. Dupont

[57] ABSTRACT

Sustained-release compositions for oral administration comprising medicament-coated nonpareils surrounded by a sustaining coating of at least three admixed polymers afford exceptionally good plasma levels of the medicament.

14 Claims, No Drawings

MEDICAMENTS IN SUSTAINED RELEASE UNIT DOSE FORM

BACKGROUND OF THE INVENTION

This invention relates to a sustained release form of a medicament for administration by the oral route.

INFORMATION DISCLOSURE STATEMENT

The use of enteric coatings on medicaments in order that the medicaments shall pass through a patient's stomach unchanged and thus ensure that the active ingredient or ingredients are released in the patient's small intestine where the pH is normally between 5 and 7.5 is now an established method of treatment. This prevents irritation of the gastrointestinal tract and is often convenient as it may make it unnecessary for a patient to take a dose of medicament more often than two or three times a day to maintain effective blood levels of medicament. A substantial number of synthetic polymeric materials have been proposed for use in such formulations, and the nature of the coatings used in the formulations have varied considerably depending upon the results sought. Thus the synthetic polymeric materials used have included polymers of vinyl monomers, such as vinyl pyrrolidone, and the semi synthetic derivatives of celluloses, such as cellulose ethers and carboxycelluloses.

For example U.S. Pat. No. 4,180,559 describes the use of hydroxypropylmethylcellulose phthalate to cause the release of an active ingredient at a pH of 5.0 to 5.5, i.e. in the duodenum, but not in the more acidic environment of the stomach. Both coated nonpareils and tablets are contemplated by the patentee, but release of the drug is apparently dependent on the coating thickness on the nonpareils.

U.S. Pat. No. 4,263,273 discloses improved forms for cardiac glycosides composed of small bodies each having a core of a pharmaceutically indifferent material, for example sugar, starch, etc. The cores are sequentially coated with successive layers of material, the first layer comprising a water soluble polymer containing the glycoside and the second layer an anionic carboxylic polymer which is difficultly soluble or insoluble at pH's below 4–7.5 but which are soluble above that range.

U.S. Pat. No. 4,367,217 discloses a sustained release form of dipyridamole comprising spheroid particles of the same or acid-addition salts thereof and an acid or an acidic substance; and a coating surrounding the spheroids comprising an acid insoluble lacquer which is soluble in the intestinal juices and a second lacquer which is insoluble in gastric and intestinal juices. The coated spheroid particles are then filled into gelatin capsules. Because of the acid nature of the medium within the sustained-release form, the dipyridamole diffuses out of the insoluble coat in the relatively alkaline environment (pH 6.0–7.0) of the intestinal juices despite the fact that the dipyridamole is insoluble at such pH levels.

U.S. Pat. No. 4,415,547 discloses a sustained-release preparation for release in the alimentary canal comprising nonpareils coated first with the drug agent, then with a water soluble drug binding substance, such as hydroxypropylmethylcellulose, and with a water insoluble film former, for example ethylcellulose. The resulting pellets are then mixed with a diluent and a binder, such as ethylcellulose, and pressed into tablets.

U.S. Pat. No. 4,248,858 discloses a sustained-release composition comprising three main components: a compressed core comprising the drug and a water soluble and a water insoluble polymer mixture; a seal coating of materials which are susceptible to hydrolysis or solution at a pH above about 5; and a sugar coating. The water soluble polymer used in the core is typically hydroxypropylmethylcellulose, and the water insoluble polymer in the core is typically ethylcellulose or a mixture of ethylcellulose and at least one of carboxypolymethylene, hydroxypropylmethylcellulose phthalate or hydroxypropylcellulose. The seal coating material used in the second layer is typically polyvinyl acetate phthalate. The compositions are said to be better absorbed in the upper portion of the alimentary tract.

U.S. Pat. No. 3,492,397 discloses the use of nonpareil beads coated with from one to ten parts of castor wax and up to one part of ethylcellulose.

U.S. Pat. No. 4,138,475 discloses the use of hard gelatine capsules containing film-coated spheroids of propanolol coated with ethylcellulose, and optionally with hydroxypropylmethylcellulose.

U.S. Pat. No. 4,361,546 discloses sustained-release compositions containing a disintegrating core comprising a medicament in a water soluble form with a water soluble coating and a plurality of non-disintegrating cores comprising the medicament in water soluble form with a coating consisting of a water insoluble film former and a water soluble polymer, the diameter of each of the disintegrating and non disintegrating cores being at least 5 mm. The compositions are said to be pH-independent.

U.S. Pat. No. 4,438,091 discloses generally the same approach as that described in U.S. Pat. No. 4,367,217 discussed above but adapted to the sustained release of bromhexine. That is, spheroid particles of an acid-addition salt of bromhexine are coated with a first lacquer, which is insoluble in gastric juices and soluble in intestinal juices, and a second lacquer, which is insoluble in gastric and intestinal juices, to produce a diffusion membrane. The coated spheroids are then packed into gelatine capsules or pressed into tablets. The lacquered membrane does not break down in the digestive tract but only allows diffusion of the drug therethrough.

U.S. Pat. No. 2,887,440 describes the use of a mixture of hydroxypropylmethylcellulose and ethylcellulose as an enteric coating, but there is no suggestion that the materials can be used to adjust the release rate of a medicament in particular pH environments.

U.S. Pat. No. 2,921,883 discloses a single coat procedure used to produce sustained-release preparations with a constant release rate composed of medicament containing pellets coated with a single coat of an intimate mixture of a solid lipid material and a solid cellulose derivative. There is no suggestion by the reference of the use of the disclosed preparations to adjust the release rates to particular pH ranges, and in fact the patent emphasizes that the compositions are not pH sensitive and are not affected by varying pH.

U.S. Pat. No. 4,369,172 discloses the use of a low viscosity grade of hydroxypropylmethylcellulose or a mixture of hydroxypropylmethylcellulose and ethylcellulose and/or sodium carboxymethylcellulose as carrier base materials combined with a medicament and shaped and compressed into a solid form for use as sustained-release preparations. There is no suggestion that the preparations can be adapted to different pH environments.

U.S. Pat. No. 4,385,078 discloses an aqueous coating composition for enteric coating of solid medicaments comprising an enterosoluble cellulose derivative, a plasticizing agent and hydroxypropylmethylcellulose or hydroxyethylcellulose as a protective colloid. The compositions are not disclosed as being adaptable to sustained release in particular pH environments. It is thus seen that the use of coated nonpareils in sustained-release preparations, as well as the use of a variety of polymeric materials to control the release of medicaments from sustained-release preparations, are known in the prior art. The prior art also discloses the concept of adapting the solubility properties of coating materials to achieve a desired release rate in a particular pH environment. However the desired release rates are achieved in prior art compositions either by use of a single coating material with a particular solubility property or by use of multiple layered coatings, each layer having its own distinct solubility/release properties. However there is no suggestion that particular admixtures of conventional coating materials, when applied as a single coating to nonpareils, can serve to provide desired release rates in particular portions of the gastrointestinal tract in order to thus produce exceptionally good bioavailability of medicaments.

It is an object of this invention to provide a sustained-release form of medicaments that are orally administered and which, by use of particular admixtures of coating materials, provide exceptionally good plasma levels of the medicaments by virtue of the solubilities of each of the materials at appropriate pH levels.

In British Pat. Specification No. 2,065,642A, there are described a number of 1,2-dihydro-3-cyano-6-lower-alkyl-5-(4-pyridinyl)-2(1H)-pyridinones which are reported to be useful as cardiotonic agents. Certain of these compounds have been found to be highly effective in human patients, but they have one important drawback, viz. that they are very readily eliminated from the human system as demonstrated by the plasma profiles obtained after administration to human patients. These compounds have been found to have much greater solubility at pH 1.5 than in the range pH 5-8.

In some instances, the solubility has been shown to be about fifty times greater at pH 1.5 than at pH 5-8.

SUMMARY OF THE INVENTION

This invention provides a sustained-release unit dosage form of a medicament of the 1,2-dihydro-3-cyano-6-lower-alkyl-5-(4-pyridinyl)-2(1H)-pyridinone class for oral administration comprising beads composed of an inert particulate core having adhered thereto a coating comprising said medicament, wherein each bead of said medicament-coated inert particulate core is surrounded by a sustaining coating comprising at least three admixed polymers, one of said polymers being soluble in gastric juices at all pH values normally encountered, a second of said polymers being insoluble in gastric juices at pH values below about 5 but soluble therein at pH values of about 5 and above and the third of said polymers being insoluble in the contents of the gastrointestinal tract at all pH values normally encountered, the three polymers being respectively present in such proportions as to permit a substantially uniform release of the medicament present notwithstanding the differing solubilities at the differing pH values prevailing during passage of the beads through the stomach and the gastrointestinal tract of a patient.

DETAILED DESCRIPTION INCLUSIVE OF THE PREFERRED EMBODIMENTS

It is preferred that the weight of the third polymer which is insoluble at all pH's in the contents of the gastrointestinal tract, be greater than the sum of the weights of the other two polymers present in the sustaining coating. A convenient ratio of the weight of the insoluble polymer to the combined weights of the other two polymers present in the sustaining layer has been found to be from about 1.5:1 to about 2:1.

The invention has been found to have a particular application to the formulation in unit dosage form for administration by the oral route of 1,2-dihydro-3-cyano-6-lower-alkyl-5-(4-pyridinyl)-2(1H)-pyridinones having the general formula:

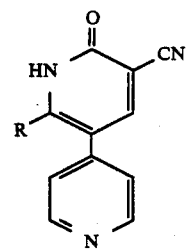

in which R is a lower-alkyl group having from 1 to 4 carbon atoms. A preferred species is 1,2-dihydro-3-cyano-6-methyl-5-(4-pyridinyl)-2(1H)-pyridinone of formula I where R is methyl. With such materials it has been found that, upon administration by the oral route, the concentration of the medicament in the plasma rises very rapidly during the first hour and then falls by approximately two-thirds of the maximum reached during the second hour. Subsequently it falls at a somewhat diminishing rate during the third and subsequent hours. If a single dose is to be sufficient to maintain effective blood levels in a patient for a substantial number of hours, e.g. 4 or 8 hours, a system needs to be devised in which only a portion of the dosage is made available for absorption into the blood at any one time. Continual release of the medicament will maintain effective blood levels until the next dose of medication is taken. The rate of dissolution (and therefore availability) has been found to be determined by the pH of the particular part of the gastrointestinal tract.

It has been found that, in the case of the pyridyl-pyridinones, the rate of dissolution is greatest in the range of lowest pH value, and the rate of dissolution decreases as the pH rises.

Consequently the particular polymers used and their proportions in the sustaining layer will determine the release characteristics of the medicament from the dosage form.

It is preferred to use nonpareils as the inert substrate material of the beads.

The substrate is then coated with particles of the medicament in solid form. It may be necessary to convert a medicament to a derivative such as a salt in order to obtain it in solid form. Medicaments available in solid form may need to be ground in order to obtain particles sufficiently small to be conveniently adhered to the particles of core material. The latter are conveniently of a size which will pass a 25 US mesh but be retained on a 30 US mesh (25–30) mesh). To adhere the particles of solid medicament to the inert substrate, it is preferred to use a water soluble pharmacologically acceptable adhesive, such as a suitable grade of hydroxypropylmethylcellulose. The hydroxypropylmethylcellulose used may be that known as "Pharmacoat 606", which is hydroxypropylmethylcellulose, a 2% solution of which has a viscosity of 6 cps. at 20° C. A thorough dispersion of the solid medicament in Pharmacoat 606 solution is then prepared and used to coat the nonpareils or other particulate inert substrate material in a coating column where the coated material is dried at a raised temperature, e.g. 40°-60° C.

The sustaining coating essentially contains three polymers each of which behaves differently in the gastrointestinal tract.

The first polymer should be soluble at all pH values normally encountered in the gastrointestinal tract. In the case of the pyridyl pyridinones this includes the pH range over which these substances exhibit their maximum solubility in the gastric juices, and when this is the case the preferred polymer is hydroxypropylmethylcellulose. Other polymers which may be used for this purpose include polyvinylpyrrolidone and sodium carboxymethylcellulose. When it is essential to reduce the dissolution rate of the medicament at pH values of the order of 1 5, the proportion of this polymer in the mixture of polymers should be kept low, e.g. 15%-20% or less by weight of the whole mixture of polymers.

The second polymer used should be one which is insoluble at pH values below about 5.0 but soluble therein at pH values of about 5 and above. The use of such a polymer ensures that, at pH values of about 5 and above, the permeability of the coat to the medicament increases, and this rise in permeability counteracts the reduced solubility of the medicament to reduce the dependence of release rate on pH.

The preferred polymer for this purpose is hydroxypropylmethylcellulose phthalate. Other polymers which are suitable for this purpose include copolymers of the lower alkyl methacrylates.

The third polymer used should be one which is insoluble at all pH values normally encountered in the gastrointestinal tract. In the lower gastrointestinal tract pH values of about 7.5 are normally to be expected, and this is the minimum value for insolubility of the third polymer. The third polymer serves to form a diffusion matrix or membrane around the medicament-coated nonpareils and allows the medicament to diffuse out of the matrix as the beads pass from a low to a higher pH environment. The preferred third polymer is ethylcellulose. Other polymers which may be used include copolymers of the lower alkyl methacrylates in which the copolymerising monomer contains a hydrophilic group.

Other factors which affect the rate of release of the medicament present include the thickness of the sustaining coating and the ratios of the three polymers present in the sustaining coating. Regarding thickness of the coating, the thicker the coating the slower the rate of release at all pH values.

The polymer ratios have an important bearing upon the rate of release of medicament at all pH values. Increase in the ratio of the first polymer to the third polymer raises the rate of release of medicament at all pH values, whilst decrease in this ratio reduces the rate of release. Increase in the ratio of the second polymer to the third polymer increases the rate of release at pH values above about 5. Increase in the ratio of the second polymer to the first polymer without changing the proportion of the third polymer decreases the rate of release at pH values below about 5.

In producing the unit dosage form of the product in accordance with the invention one may, for example, add 18 parts by weight of the three selected polymers to 261 parts by weight of a dispersion medium therefor. When the three polymers are cellulose ethers and ether esters, ethanol is a suitable medium. The resulting mixture is stirred until well dispersed, and a low boiling solvent (e.g. methylene chloride) is then added and stirring continued until a clear solution is obtained. Nonpareils coated with medicaments are placed in a coating column or pan, and the solution of the three polymers is then gradually fed into the column or pan whilst passing a current of warm air through the nonpareils until dry coated nonpareils are obtained.

The dried coated nonpareils are then assayed and weighed into unit dosage quantities, separate weighed quantities are fed into hard gelatine capsules, and each capsule is closed.

A preferred formulation within the ambit of the invention comprises nonpareils coated with 1,2-dihydro-3-cyano-6-methyl-5-(4-pyridinyl)-2(1H)-pyridinone with a sustaining coating comprising hydroxypropylmethylcellulose, hydroxypropylmethylcellulose phthalate and ethylcellulose.

The following examples illustrate the invention. All parts are by weight.

PREPARATION A

Preparation of Nonpareils Coated with Medicament 11 parts of hydroxypropylmethylcellulose (6 centpoises) (Here and elsewhere in this patent the viscosities reported are obtained in 2% aqueous solution at 20° C.) were suspended in 111 parts of purified water previously heated to boiling. 440 additional parts of water were then added to the suspension and the whole stirred until a diluted Pharmacoat suspension had formed.

11 parts of 1,2 dihydro-3-cyano-6-methyl-5-(4-pyridinyl)-2(1H)-pyridinone were stirred into the Pharmacoat suspension until well dispersed. 200 parts of nonpareils (sugar/starch base: 25–30 mesh) were placed in a coating column or pan and, whilst passing an atomizing current of warm air therethrough, the diluted Pharmacoat suspension was gradually added. After all the Pharmacoat suspension had been added, the passage of the current of warm air was continued until the coated nonpareils were dry.

EXAMPLE 1

In a suitable container were placed 261 parts of ethanol, 11.70 parts of ethylcellulose, 3.60 parts of hydroxypropylmethylcellulose and 2.70 parts of hydroxypropylmethylcellulose phthalate. The solids were stirred in until well dispersed, and 621 parts of methylene chloride were then added to the dispersion. A clear solution should result.

Into a coating column or pan were placed 222 parts of coated nonpareils prepared as described above in Preparation A. Whilst passing an atomising current of warm air through the column, the clear solution described above was gradually fed into the coating column or pan. After all the solution had been introduced into the column or pan, the passage of warm air was continued until the nonpareils were dry.

The product, consisting of nonpareils first coated with medicament and then coated with sustaining coating of three polymers, was then removed from the column and, after cooling to room temperature, weighed out into portions, each containing the required quantity of medicament, and separately fed into standard hard gelatine capsules and closed.

EXAMPLE 2

272.72 parts of nonpareils (25–30 mesh) were coated with a dispersion prepared from 15.0 parts of 1,2-dihydro-3-cyano-6-methyl-5-(4-pyridinyl)-2(1H)-pyridinone and 15.0 parts of hydroxypropylmethylcellulose (6 centipoises) as described in Preparation A.

A sustaining coating solution was prepared from 6 parts of ethylcellulose, 2 parts of hydroxypropylmethylcellulose (6 centipoises) and 2 parts of hydroxypropylmethylcellulose phthalate, the solution was used to coat the medicament-coated nonpareils, and the thus coated beads were assayed weighed out and fed into hard gelatine capsules all as described in Example 1.

EXAMPLE 3

Nonpareils were coated with 1,2-dihydro-3-cyano-6-methyl-5-(4-pyridinyl)-2(1H)-pyridinones as described in Example 2. A sustaining coating solution was then prepared from 12.42 parts of ethylcellulose, 4.14 parts of hydroxypropylmethylcellulose (6 centipoises) and 4.14 parts of hydroxypropylmethylcellulose phthalate which was applied to the nonpareils, and the coated beads were assayed weighed out and fed into hard gelatine capsules as described in Example 1.

EXAMPLE 4

Nonpareils were coated with 1,2-dihydro-3-cyano-6-methyl-5-(4-pyridinyl)-2(1H)-pyridinone as described in Example 2. A sustaining coating solution was then prepared from 15.95 parts of ethylcellulose, 4.91 parts of hydroxypropylmethylcellulose and 3.68 parts of hydroxypropylmethylcellulose phthalate which was applied to the nonpareils, and the coated beads were assayed, weighed out and fed into hard gelatine capsules as described in Example 1.

EXAMPLE 5

114 parts of nonpareils (passing 25 or 30 mesh) were coated with a dispersion prepared from 15 parts of 1,2-dihydro-3-cyano-6-methyl-5-(4-pyridinyl)-2(1H)-pyridinone and 6.0 parts of hydroxypropylmethylcellulose (6 centipoises) as described in Preparation A. A sustaining coating solution was prepared from 6 parts of ethylcellulose, parts of hydroxypropylmethylcellulose (6 centipoises) and 2 parts of hydroxypropylmethylcellulose phthalate, the solution was used to coat the medicament-coated nonpareils, and the thus coated beads were assayed, weighed out and fed into hard gelatine capsules all as described in Example 1.

EXAMPLE 6

Nonpareils were coated with 1,2-dihydro-3-cyano-6-methyl-5-(4-pyridinyl)-2(1H)-pyridinone as described in Example 5. A sustaining coating solution was then prepared from 6.0 parts of ethylcellulose, 1.90 parts of hydroxypropylmethylcellulose (6 centipoises) and 2.10 parts of hydroxypropylmethylcellulose phthalate, the solution was used to coat the medicament-coated nonpareils, and the thus coated beads were assayed, weighed out and fed into hard gelatine capsules all as described in Example 1.

COMPARISON FORMULATIONS

For purposes of comparing the bioavailability properties of compositions prepared in accordance with the present invention containing 1,2-dihydro-3-cyano-6-methyl-5-(4-pyridinyl)-2(1H)-pyridinone as the active ingredient, with the bioavailability properties of a conventional film coated caplet formulation and two sustained release tablet formulations, four formulations, each containing 1,2-dihydro-3-cyano-6-methyl-5-(4-pyridinyl)-2(1H)-pyridinone, designated Comparative Formulations A-1, A-2, B, and C, comprising, respectively, caplets containing 5 mg. of active ingredient (Comp. Form. A-1); caplets containing 10 mg. of active ingredient (Comp. Form. A-2); sustained-release tablets containing 15 mg. of active ingredient (Comp. Form B); and sustained-release tablets containing 15 mg. of active ingredient (Comp. Form. C);

were formulated as follows, all parts being expressed as parts by weight:

|  | Comparative Formulations | | | |
| --- | --- | --- | --- | --- |
|  | A-1 | A-2 | B | C |
| Active Ingredient | 5.0 | 10.0 | 15.0 | 15.0 |
| Lactose B.P. | 104.50 | 209.00 | — | — |
| Lactose (Regular hydrous U.S.P.) | — | — | 205.5 | 193.5 |
| Starch | 40.0 | 80.0 | — | — |
| Cellulose (microcrystalline) | 50.0 | 100.0 | — | — |
| Magnesium Stearate | 0.50 | 1.0 | 1.5 | 1.5 |
| Hydroxypropylmethylcellulose (15 cps) | 3.70 | 8.33 | — | — |
| Glyceryl triacetate | 0.739 | 1.67 | — | — |
| Titanium dioxide | 1.48 | — | — | — |
| Dyes | 0.0835 | 0.235 | — | — |
| Magnesium hydroxide | — | — | 15.0 | 15.0 |
| Hydroxypropylmethyl cellulose (4000 cps/20° C.) | — | — | 63.0 | 25.0 |
| Hydroxypropylmethyl cellulose (1000 cps/20° C.) | — | — | — | 50.0 |

Comparative Formulations A-1, A-2, B and C were formulated and pressed into caplets or tablets using well known tabletting procedures.

A comparative bioavailability study of each of Formulations A-1, A-2, B, and C, and the nonpareils containing capsule formulation of Examples 5 and 6 above was carried out in ten male volunteers, ages 23–37, on a randomized, cross-over basis in five parts acccording to the following schedule:

|  | Formulation | | | | |
| --- | --- | --- | --- | --- | --- |
| Volunteer | Part 1 | Part 2 | Part 3 | Part 4 | Part 5 |
| 1. NH | D | E | A | B | C |
| 2. CD | C | E | B | D | A |
| 3. NH | B | D | A | C | E |
| 4. SW | D | A | C | E | B |
| 5. SK | E | B | D | A | C |
| 6. AL | C | D | E | A | B |
| 7. PM | B | C | D | E | A |
| 8. DW | A | C | E | B | D |
| 9. TW | A | B | C | D | E |
| 10. HL | E | A | B | C | D | where the formulations administered are identified as follows, reference in the second column being made to the comparative formulations and the formulation of Example 7 described above:

| Formulation | Corresponds to |
|---|---|
| A | 1 caplet of Formulation A-1 plus 1 caplet of Formulation A-2 (15 mg. total) |
| B | 1 tablet of Formulation B |
| C | 1 tablet of Formulation C |
| D | 1 capsule of the formulation of Example |
| E | 1 capsule of the formulation of Example 6 |

Each dosage thus contained 15 mg. of the active medicament and was administered with 200 ml. of tap water. Blood samples were taken pre-medication and at 10, 20, 30 and 45 minutes and 1.0, 1.5, 2.0, 2.5, 3.0, 3.5, 4.0, 5.0, 6.0, 8.0, 11.0, 14.0 and 24.0 hours post-medication. Prepared plasma samples were stored below $-15°$ C. pending assay for the active ingredient by a validated HPLC procedure.

Urine samples were collected pre-medication and over the 0–24 hour post-medication period. After measuring volume and pH, aliquots were stored below $-15°$ C. pending assay for the active ingredient by a validated HPLC procedure.

Regression analysis of peak area ratios (active ingredient/internal standard) with respect to concentration was performed for known calibration standards made up in control plasma. The resulting linear regression was used to determine the plasma concentrations of the active ingredient from the volunteer samples. The data so obtained with each of Formulations A-E for each of the ten volunteers are given in Tables 1-5. In the tables which follow, S.D. represents Standard Deviation, and C of V represents Coefficient of Variation.

TABLE 1

(Formulation A-15 mg.)

| Volunteer | 0.00 | 0.17 | 0.33 | 0.50 | 0.75 | 1.0 | 1.5 | 2.0 | 2.5 | 3.0 | 3.5 | 4.0 | 5.0 | 6.0 | 8.0 | 11.0 | 14.0 | 24.0 |
|---|---|---|---|---|---|---|---|---|---|---|---|---|---|---|---|---|---|---|
| 1. NH | ND | 32 | 190 | 409 | 440 | 380 | 215 | 134 | 75 | 46 | 30 | 19 | 13 | 8 | 5 | ND | ND | ND |
| 2. CD | ND | ND | 50 | 281 | 348 | 284 | 182 | 100 | 57 | 42 | 29 | 19 | 9 | 3 | ND | ND | ND | ND |
| 3. CH | ND | 62 | 462 | 528 | 465 | 363 | 243 | 134 | 91 | 55 | 35 | 26 | 15 | 10 | 4 | ND | ND | ND |
| 4. SW | ND | 22 | 132 | 371 | 473 | 363 | 205 | 126 | 87 | 55 | 37 | 29 | 20 | 10 | ND | ND | ND | ND |
| 5. SK | ND | 120 | 359 | 312 | 270 | 221 | 154 | 89 | 60 | 38 | 32 | 25 | 20 | 15 | 10 | ND | ND | ND |
| 6. AL | ND | ND | 36 | 72 | 226 | 239 | 291 | 238 | 166 | 108 | 64 | 43 | 26 | 13 | 7 | 4 | ND | ND |
| 7. PM | ND | 10 | 363 | 353 | 306 | 234 | 150 | 93 | 69 | 55 | 34 | 23 | 13 | 8 | 6 | ND | ND | ND |
| 8. DW | ND | 9 | 219 | 347 | 306 | 232 | 160 | 109 | 82 | 58 | 39 | 27 | 15 | 11 | 8 | 7 | ND | ND |
| 9. TW | ND | 8 | 104 | 370 | 439 | 314 | 182 | 106 | 64 | 37 | 32 | 20 | 11 | 6 | 6 | ND | ND | ND |
| 10. HL | ND | 10 | 291 | 636 | 508 | 438 | 301 | 182 | 123 | 86 | 56 | 34 | 24 | 9 | 3 | 1 | ND | ND |
| Mean | — | 27 | 220 | 368 | 378 | 307 | 208 | 131 | 87 | 58 | 39 | 27 | 17 | 9 | 5 | 1 | 0 | 0 |
| S.D. | — | 37 | 145 | 148 | 98 | 76 | 55 | 46 | 33 | 22 | 12 | 7 | 6 | 3 | 3 | 2 | 0 | 0 |
| C of V | — | 137 | 65 | 40 | 26 | 24 | 26 | 35 | 38 | 38 | 30 | 28 | 33 | 36 | 66 | 199 | 0 | 0 |

TABLE 2

(Formulation B-15 mg.)

| Volunteer | 0.00 | 0.17 | 0.33 | 0.50 | 0.75 | 1.0 | 1.5 | 2.0 | 2.5 | 3.0 | 3.5 | 4.0 | 5.0 | 6.0 | 8.0 | 11.0 | 14.0 | 24.0 |
|---|---|---|---|---|---|---|---|---|---|---|---|---|---|---|---|---|---|---|
| 1. NH | ND | ND | 13 | 11 | 37 | 81 | 96 | 66 | 55 | 56 | 54 | 47 | 39 | 35 | 20 | 19 | 18 | 10 |
| 2. CD | ND | ND | 20 | 50 | 71 | 79 | 85 | 90 | 73 | 80 | 68 | 49 | 30 | 16 | 15 | 13 | 7 | 6 |
| 3. CH | ND | ND | 12 | 18 | 16 | 38 | 141 | 149 | 98 | 71 | 67 | 56 | 42 | 27 | 19 | 16 | 7 | 5 |
| 4. SW | ND | ND | 18 | 34 | 39 | 48 | 85 | 60 | 56 | 80 | 40 | 31 | 21 | 12 | 9 | 11 | 5 | ND |
| 5. SK | ND | ND | 14 | 32 | 49 | 65 | 100 | 119 | 137 | 103 | 73 | 50 | 29 | 22 | 19 | 12 | 8 | 5 |
| 6. AL | ND | ND | 33 | 54 | 59 | 61 | 53 | 60 | 66 | 65 | 55 | 49 | 32 | 25 | 25 | 24 | 14 | 9 |
| 7. PM | ND | ND | 27 | 58 | 73 | 64 | 45 | 34 | 45 | 47 | 43 | 40 | 37 | 30 | 19 | 15 | 11 | 8 |
| 8. DW | ND | 4 | 22 | 40 | 49 | 38 | 37 | 27 | 34 | 59 | 59 | 40 | 32 | 22 | 8 | 12 | 7 | 8 |
| 9. TW | ND | 16 | 36 | 41 | 61 | 56 | 41 | 27 | 30 | 22 | 15 | 13 | 13 | 7 | 11 | 25 | 12 | ND |
| 10. HL | ND | 10 | 34 | 55 | 64 | 61 | 68 | 71 | 72 | 71 | 66 | 53 | 43 | 31 | 29 | 24 | 15 | 11 |
| Mean | — | 3 | 23 | 39 | 52 | 59 | 75 | 70 | 67 | 65 | 54 | 43 | 32 | 23 | 17 | 17 | 10 | 6 |
| S.D. | — | 6 | 9 | 16 | 18 | 15 | 33 | 40 | 32 | 21 | 17 | 13 | 9 | 9 | 7 | 5 | 4 | 4 |
| C of V | — | 186 | 39 | 40 | 33 | 25 | 43 | 56 | 47 | 33 | 32 | 29 | 29 | 38 | 38 | 32 | 41 | 61 |

TABLE 3

(Formulation C-15 mg.)

| Volunteer | 0.00 | 0.17 | 0.33 | 0.50 | 0.75 | 1.0 | 1.5 | 2.0 | 2.5 | 3.0 | 3.5 | 4.0 | 5.0 | 6.0 | 8.0 | 11.0 | 14.0 | 24.0 |
|---|---|---|---|---|---|---|---|---|---|---|---|---|---|---|---|---|---|---|
| 1. NH | ND | 5 | 27 | 50 | 93 | 115 | 164 | 126 | 100 | 73 | 97 | 69 | 37 | 26 | 11 | 11 | 5 | 2 |
| 2. CD | ND | ND | 34 | 62 | 71 | 78 | 86 | 103 | 98 | 70 | 57 | 39 | 20 | 17 | 7 | 3 | ND | ND |
| 3. CH | ND | ND | 16 | 58 | 118 | 97 | 116 | 161 | 167 | 188 | 146 | 108 | 56 | 37 | 21 | 11 | ND | ND |
| 4. SW | ND | 6 | 24 | 42 | 43 | 84 | 115 | 86 | 126 | 133 | 86 | 61 | 37 | 26 | 12 | 7 | ND | ND |
| 5. SK | ND | ND | 20 | 45 | 64 | 116 | 112 | 75 | 41 | 40 | 31 | 27 | 34 | 33 | 19 | 5 | ND | ND |
| 6. AL | ND | ND | 8 | 13 | 33 | 47 | 123 | 146 | 123 | 126 | 105 | 81 | 72 | 50 | 21 | 9 | ND | 7 |
| 7. PM | ND | ND | 38 | 51 | 44 | 49 | 53 | 77 | 85 | 59 | 56 | 38 | 19 | 10 | 7 | 4 | 2 | 2 |
| 8. DW | ND | 2 | 38 | 61 | 62 | 55 | 54 | 55 | 76 | 69 | 63 | 45 | 31 | 23 | 14 | 8 | 3 | 2 |
| 9. TW | ND | 6 | 51 | 98 | 108 | 94 | 54 | 47 | 56 | 55 | 40 | 39 | 22 | 18 | 10 | 10 | 6 | ND |
| 10. HL | ND | ND | 51 | 66 | 53 | 51 | 59 | 57 | 61 | 57 | 62 | 71 | 48 | 36 | 25 | 20 | 17 | 14 |
| Mean | — | 2 | 31 | 55 | 69 | 79 | 94 | 93 | 93 | 87 | 74 | 58 | 38 | 28 | 15 | 9 | 3 | 3 |
| S.D. | — | 3 | 14 | 21 | 29 | 27 | 38 | 40 | 38 | 47 | 34 | 25 | 17 | 12 | 6 | 5 | 5 | 5 |
| C of V | — | 141 | 46 | 39 | 41 | 34 | 40 | 42 | 40 | 54 | 46 | 43 | 45 | 42 | 43 | 55 | 161 | 184 |

TABLE 4

(Formulation D-15 mg.)

| Volunteer | 0.00 | 0.17 | 0.33 | 0.50 | 0.75 | 1.0 | 1.5 | 2.0 | 2.5 | 3.0 | 3.5 | 4.0 | 5.0 | 6.0 | 8.0 | 11.0 | 14.0 | 24.0 |
|---|---|---|---|---|---|---|---|---|---|---|---|---|---|---|---|---|---|---|
| 1. NH | ND | ND | ND | 9 | ND | 8 | 151 | 126 | 108 | 106 | 137 | 107 | 79 | 54 | 18 | 5 | 4 | ND |
| 2. CD | ND | ND | ND | 7 | 21 | 55 | 74 | 96 | 153 | 158 | 111 | 78 | 36 | 25 | 14 | 10 | 8 | ND |
| 3. CH | ND | ND | ND | ND | 18 | 71 | 96 | 113 | 148 | 162 | 123 | 98 | 58 | 37 | 19 | 11 | 10 | 9 |
| 4. SW | ND | ND | ND | ND | 22 | 59 | 77 | 85 | 156 | 136 | 104 | 45 | 51 | 37 | 15 | 7 | ND | ND |
| 5. SK | ND | ND | ND | ND | 21 | 44 | 66 | 101 | 102 | 82 | 64 | 51 | 42 | 29 | 17 | 5 | ND | ND |
| 6. AL | ND | ND | ND | ND | 8 | 27 | 48 | 83 | 175 | 146 | 134 | 104 | 57 | 35 | 14 | 5 | 1 | 1 |
| 7. PM | ND | ND | 6 | 10 | 18 | 23 | 36 | 59 | 65 | 67 | 74 | 61 | 36 | 26 | 19 | 10 | 8 | 8 |
| 8. DW | ND | ND | ND | ND | ND | 14 | 135 | 104 | 95 | 118 | 111 | 82 | 52 | 36 | 19 | 9 | 7 | 8 |
| 9. TW | ND | ND | ND | ND | 7 | 21 | 83 | 91 | 110 | 108 | 78 | 51 | 30 | 19 | 14 | 32 | 6 | ND |
| 10. HL | ND | ND | 7 | 11 | 41 | 54 | 80 | 107 | 127 | 135 | 119 | 90 | 74 | 54 | 23 | 18 | 12 | 7 |
| Mean | — | — | 1 | 4 | 16 | 38 | 85 | 97 | 124 | 122 | 106 | 77 | 52 | 35 | 17 | 11 | 6 | 3 |
| S.D. | — | — | 3 | 5 | 12 | 22 | 35 | 19 | 34 | 31 | 25 | 23 | 16 | 12 | 3 | 8 | 4 | 4 |
| C of V | — | — | 211 | 131 | 79 | 57 | 41 | 19 | 27 | 25 | 24 | 30 | 31 | 33 | 17 | 74 | 75 | 123 |

TABLE 5

(Formulation E-15 mg.)

| Volunteer | 0.00 | 0.17 | 0.33 | 0.50 | 0.75 | 1.0 | 1.5 | 2.0 | 2.5 | 3.0 | 3.5 | 4.0 | 5.0 | 6.0 | 8.0 | 11.0 | 14.0 | 24.0 |
|---|---|---|---|---|---|---|---|---|---|---|---|---|---|---|---|---|---|---|
| 1. NH | ND | ND | ND | ND | ND | 8 | 82 | 106 | 105 | 111 | 120 | 97 | 68 | 49 | 18 | 9 | 7 | ND |
| 2. CD | ND | ND | ND | ND | 8 | 33 | 64 | 87 | 105 | 88 | 62 | 55 | 35 | 23 | 14 | 11 | ND | 6 |
| 3. CH | ND | ND | ND | ND | 28 | 92 | 186 | 159 | 203 | 177 | 142 | 113 | 60 | 37 | 17 | 51 | 4 | 3 |
| 4. SW | ND | ND | ND | ND | 8 | 14 | 42 | 78 | 154 | 140 | 143 | 133 | 104 | 58 | 24 | 10 | ND | ND |
| 5. SK | ND | ND | ND | ND | 4 | 13 | 58 | 102 | 124 | 109 | 83 | 60 | 39 | 27 | 18 | 12 | 5 | ND |
| 6. AL | ND | ND | ND | ND | 23 | 39 | 66 | 108 | 143 | 150 | 154 | 126 | 85 | 42 | 16 | 6 | 4 | ND |
| 7. PM | ND | ND | ND | 8 | 36 | 66 | 75 | 65 | 75 | 89 | 71 | 60 | 38* | 26 | 16 | 8 | 7 | 8 |
| 8. DW | ND | ND | ND | ND | 13 | 25 | 34 | 61 | 130 | 168 | 116 | 71 | 44 | 30 | 16 | 9 | 5 | 5 |
| 9. TW | ND | ND | ND | 6 | 25 | 47 | 84 | 107 | 123 | 100 | 72 | 54 | 36 | 28 | 16 | 12 | 7 | ND |
| 10. HL | ND | ND | ND | 7 | 17 | 27 | 51 | 69 | 104 | 114 | 111 | 135 | 91 | 68 | 37 | 32 | 17 | 10 |
| Mean | — | — | — | 2 | 16 | 36 | 74 | 94 | 127 | 125 | 107 | 90 | 60 | 39 | 19 | 16 | 6 | 3 |
| S.D. | — | — | — | 3 | 12 | 26 | 43 | 29 | 35 | 32 | 34 | 34 | 26 | 15 | 7 | 14 | 5 | 4 |
| C of V | — | — | — | 162 | 71 | 71 | 57 | 30 | 27 | 25 | 31 | 37 | 43 | 39 | 35 | 89 | 85 | 119 |

*Estimated

Plasma concentrations of the active ingredient from each of Formulations A-E in the foregoing study were processed using the bioavailability program "BIOMU". From an input of plasma concentrations by volunteers, part classification and cross-over design, the program produces tables of data according to formulation, identifies the maximum plasma concentration ($C_{max}$) and the time to reach maximum concentration ($t_{max}$). Results so obtained are given in Table 6.

the maximum plasma concentrations are reached later. However, more significantly, it will be seen that the formulations of the invention (Formulations D and E) not only produce an equal or greater maximum plasma concentration than the other sustained-release preparations (Formulations B-C), they also produce a more prolonged release time than any of the others.

The area under the plasma concentration vs. time profile (AUC) from zero time to the last sampling point

TABLE 6

| | Formulation A | | Formulation B | | Formulation C | | Formulation D | | Formulation E | |
|---|---|---|---|---|---|---|---|---|---|---|
| Volunteer | $C_{max}$ | $t_{max}$ | $C_{max}$ | $t_{max}$ | $C_{max}$ | $t_{max}$ | $C_{max}$ | $t_{max}$ | $C_{max}$ | $t_{max}$ |
| 1. NH | 440 | 0.75 | 96 | 1.50 | 164 | 1.50 | 151 | 1.50 | 120 | 3.50 |
| 2. CD | 348 | 0.75 | 90 | 2.00 | 103 | 2.00 | 158 | 3.00 | 105 | 2.50 |
| 3. CH | 528 | 0.50 | 149 | 2.00 | 188 | 3.00 | 162 | 3.00 | 203 | 2.50 |
| 4. SW | 473 | 0.75 | 85 | 1.50 | 133 | 3.00 | 156 | 2.50 | 154 | 2.50 |
| 5. SK | 359 | 0.33 | 137 | 2.50 | 116 | 1.00 | 102 | 2.50 | 124 | 2.50 |
| 6. AL | 291 | 1.50 | 66 | 2.50 | 146 | 2.00 | 175 | 2.50 | 154 | 3.50 |
| 7. PM | 363 | 0.33 | 73 | 0.75 | 85 | 2.50 | 74 | 3.50 | 89 | 3.00 |
| 8. DW | 347 | 0.50 | 59 | 3.50 | 76 | 2.50 | 135 | 1.50 | 168 | 3.00 |
| 9. TW | 439 | 0.75 | 61 | 0.75 | 108 | 0.75 | 110 | 2.50 | 123 | 2.50 |
| 10. HL | 636 | 0.50 | 72 | 2.50 | 71 | 4.00 | 135 | 3.00 | 135 | 4.00 |
| Mean | 422 | 0.67 | 89 | 1.95 | 119 | 2.23 | 1.36 | 2.55 | 138 | 2.95 |
| S.D. | 103 | 0.34 | 31 | 0.90 | 39 | 0.99 | 32 | 0.64 | 33 | 0.55 |
| C of V | 24.5 | 50.9 | 35 | 43.9 | 32 | 44.5 | 23 | 25.2 | 24 | 18.7 |

These data show that, while a conventional nonsustained release formulation, as represented by Formulation A, reaches a much higher blood plasma concentration than any of the sustained-release formulations represented by Formulations B-E, the maximum concentration is reached very rapidly (less than 1 hour).

Each of the sustained-release preparations (Formulations B-E) produce lower plasma concentrations, but gives a measure of the total medicament plasma concentration, or total bioavailability, of the medicament and is calculated using the trapezoidal rule. A measure of relative bioavailability was obtained by calculating the $AUC^{24}_0$ value for each of Formulations B-E as a percentage of the $AUC^{24}_0$ obtained from an equivalent dose of a conventional caplet, as represented by Formulation A. These data are given in Table 7.

TABLE 7

| Volunteer | Formulation A AUC$_0^{24}$ | Formulation B AUC$_0^{24}$ | % R.B. | Formulation C AUC$_0^{24}$ | % R.B. | Formulation D AUC$_0^{24}$ | % R.B. | Formulation E AUC$_0^{24}$ | % R.B. |
|---|---|---|---|---|---|---|---|---|---|
| 1. NH | 677 | 608 | 90 | 593 | 88 | 645 | 95 | 597 | 88 |
| 2. CD | 494 | 502 | 102 | 374 | 76 | 572 | 116 | 426 | 86 |
| 3. CH | 788 | 578 | 73 | 748 | 95 | 730 | 93 | 912 | 116 |
| 4. SW | 669 | 349 | 52 | 502 | 75 | 505 | 75 | 667 | 100 |
| 5. SK | 568 | 572 | 101 | 388 | 68 | 411 | 72 | 482 | 85 |
| 6. AL | 708 | 581 | 82 | 664 | 94 | 554 | 78 | 657 | 93 |
| 7. PM | 558 | 482 | 86 | 326 | 58 | 457 | 82 | 456 | 82 |
| 8. DW | 591 | 384 | 65 | 392 | 66 | 614 | 104 | 534 | 90 |
| 9. TW | 584 | 335 | 57 | 390 | 67 | 511 | 88 | 508 | 87 |
| 10. HL | 922 | 658 | 71 | 661 | 72 | 765 | 83 | 884 | 96 |
| Mean | 656 | 505 | 78 | 504 | 76 | 576 | 89 | 612 | 92 |
| S.D. | 127 | 115 | 17 | 151 | 13 | 114 | 14 | 170 | 10 |
| C of V | 19 | 23 | 22 | 30 | 17 | 20 | 16 | 28 | 11 |

These data show that Formulations D and E, prepared in accordance with the invention, provide greater bioavailability than the other sustained-release preparations relative to the conventional caplet formulation represented by Formulation A.

Regression analysis of peak height ratios (active ingredient/internal standard) with respect to concentration was performed for known calibration standards in control urine. The resulting linear regression was used to determine urine concentrations of the active ingredient in each sample. Recovered amounts of the active ingredient were then calculated from the urine volume for the collection period of each sample. Data so obtained, expressed as percent of dose administered, are given in Table 8.

TABLE 8

| Volunteer | Formulation A mg | % dose | Formulation B mg | % dose | Formulation C mg | % dose | Formulation D mg | % dose | Formulation E mg | % dose |
|---|---|---|---|---|---|---|---|---|---|---|
| 1. NH | 12.6 | 84 | 10.1 | 67 | 6.86 | 46 | 12.4 | 83 | 11.7 | 78 |
| 2. CD | 10.3 | 69 | 12.2 | 81 | 10.4 | 69 | 11.2 | 75 | 8.41 | 56 |
| 3. CH | 12.1 | 81 | 7.92 | 53 | 7.14 | 48 | 7.72 | 51 | 8.08 | 54 |
| 4. SW | 11.1 | 74 | 7.53 | 50 | 11.7 | 78 | 9.47 | 63 | 12.2 | 81 |
| 5. SK | 13.7 | 91 | 10.9 | 73 | 7.72 | 51 | 11.2 | 75 | 9.99 | 67 |
| 6. AL | 12.3 | 82 | 7.96 | 53 | 9.01 | 60 | 13.4 | 89 | 12.3 | 82 |
| 7. PM | 13.5 | 90 | 9.28 | 62 | 9.99 | 67 | 9.79 | 65 | 8.97 | 60 |
| 8. DW | 7.4 | 49 | 6.24 | 42 | 8.29 | 55 | 9.99 | 67 | 8.70 | 58 |
| 9. TW | 10.9 | 73 | 7.10 | 47 | 8.53 | 57 | 8.06 | 54 | 8.49 | 57 |
| 10. HL | 13.6 | 91 | 8.46 | 56 | 7.62 | 51 | 9.33 | 62 | 2.04 | 14 |
| Mean | 11.8 | 78 | 8.77 | 58 | 8.73 | 58 | 10.3 | 68 | 9.87 | 66 |
| S.D. | 1.93 | 13 | 1.84 | 12 | 1.56 | 10 | 1.80 | 12.1 | 1.74 | 11.5 |
| C of V | 16 | 16 | 21 | 21 | 18 | 18 | 18 | 18 | 18 | 17 |

Since the active ingredient in each of the test formulations, 1,2-dihydro-3-cyano-6-methyl-5-(4-pyridinyl)-2(1H)-pyridinone, is only slightly metabolized and is excreted in the urine, an additional measure of bioavailability of the sustained-release preparations, including the sustained-release preparation of the invention represented by Formulations D and E, was obtained by expressing the urinary recovery of free active ingredient as a percentage of the urinary recovery from the conventional caplet represented by Formulation A. Data so obtained are given in Table 9:

TABLE 9

| Volunteer | Formulation B | C | D | E |
|---|---|---|---|---|
| 1. NH | 80 | 55 | 99 | 93 |
| 2. CD | 117 | 100 | 109 | 81 |
| 3. CH | 65 | 59 | 63 | 67 |
| 4. SW | 68 | 105 | 85 | 109 |
| 5. SK | 80 | 56 | 82 | 74 |
| 6. AL | 65 | 73 | 109 | 100 |

TABLE 9-continued

| Volunteer | Formulation B | C | D | E |
|---|---|---|---|---|
| 7. PM | 69 | 74 | 72 | 67 |
| 8. DW | 86 | 112 | 137 | 118 |
| 9. TW | 64 | 78 | 74 | 78 |
| 10. HL | 62 | 56 | 68 | 15 |
| Mean | 76 | 77 | 90 | 87 |
| S.D. | 17 | 22 | 23 | 18.5 |
| C of V | 22 | 28 | 26 | 21 |

These data show that the nonpareils-based sustained release preparations represented by Formulations D and E are approximately equivalent to one another in providing bioavailability, and both provide substantially greater bioavailability levels than the sustained release tablet formulations (Formulations B and C).

Other nitriles having the general formula I can be prepared in sustained-release form by proceeding in the same manner as that illustrated in the above examples, and the method is applicable to other solid medicaments which have an elimination half-life of the order of 0.5 to 4 hours and which can be applied to a core such as a nonpareil. In addition to cores formed of one or more normally crystalline sugars, with or without cellulose, inorganic materials such as calcium phosphate may be used as the core material.

The availability of sustained release formulations in accordance with this invention is of great assistance to the patient, since the formulations ensure that a patient would not need a unit dosage as frequently as would otherwise be the case to maintain effective blood levels of medicament. This minimizes the risk of omission to take a dose at the correct time, and it also avoids the need to take a dose during the night.

The action of the controlled in vivo release resulting from the use of the formulations in accordance with the invention results in controlled and reproducible therapy by reducing the difference in peak and trough plasma levels of patients taking the prescribed medicament. Such peaks and troughs are otherwise readily observable with a rapidly absorbed medicament having as short an elimination half-life period as 1 to 3 hours. A continuous release of medicament during passage through the stomach and the gastrointestinal tract is secured by the use of three polymers as described, and this is effected by use of a single coating operation with an admixture of polymers.

We claim:

1. A sustained release pharmaceutical composition for oral administration containing, as the active ingredient, a medicament of the formula:

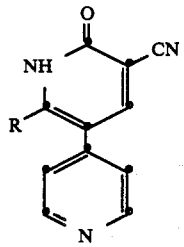

where R is lower-alkyl having from 1 to 4 carbon atoms which comprises a plurality of beads each composed of an inert particulate core having adhered thereto a coating comprising particles of said medicament and further coated with a sustaining coating comprising three admixed polymers, the first said polymer being soluble at all pH values of 1.5 and above, the second said polymer being insoluble in gastric juices at pH values below about 5 but soluble therein at pH values of about 5 and above and the third said polymer being insoluble in the contents of the gastrointestinal tract at all pH values normally encountered therein, and wherein the ratio of the weight of the third polymer to the combined weight of the other two polymers is about 1.5:1 to about 2:1.

2. A pharmaceutical composition according to claim 1 wherein said first polymer constitutes about 15–20 wt. % of the polymer mixture forming the sustaining coating.

3. A pharmaceutical composition according to claim 2 wherein the inert cores of the beads are in the form of nonpareils.

4. A pharmaceutical composition according to claim 3 wherein said first polymer is selected from hydroxypropylmethylcellulose, sodium carboxymethyl cellulose and polyvinylpyrrolidone.

5. A pharmaceutical composition according to claim 4 wherein said second polymer is hydroxypropylmethylcellulose phthalate.

6. A pharmaceutical composition according to claim 5 wherein said third polymer is ethyl cellulose.

7. A pharmaceutical composition according to claim 6 wherein said first polymer is hydroxypropylmethylcellulose and wherein the ratio of the weight of the ethylcellulose to the combined weight of the hydroxypropylmethylcellulose and the hydroxypropylmethylcellulose phthalate is about 1.5:1.

8. A pharmaceutical composition according to claim 6 wherein said medicament is 1,2-dihydro-3-cyano-6-methyl-5-(4-pyridinyl)-2(1H)-pyridinone.

9. A pharmaceutical composition according to claim 8 in unit dosage form contained within a gelatine capsule.

10. A process for producing a pharmaceutical composition according to claim 1 which comprises: (1) coating inert core particles with particles of said medicament and a binder for adhering said medicament particles to said core particles and (2) applying to said coated core particles a sustaining coating solution comprising three admixed polymers, the first said polymer being soluble at all pH values of 1.5 and above, the second said polymer being insoluble in gastric juices at pH values below about 5 but soluble therein at pH values of about 5 and above and the third said polymer being insoluble in the contents of the gastrointestinal tract at all pH values normally encountered therein, and wherein the ratio of the weight of the third polymer to the combined weight of the other two polymers is about 1.5:1 to about 2:1.

11. A process according to claim 10 wherein said sustaining coating is formed by applying to the medicament-coated core particles a solution of said three polymers in a volatile solvent therefor and evaporating the solvent from the particles thus coated.

12. A process according to claim 11 wherein said solution is produced by forming a dispersion of the three polymers in a suitable medium, adding a lower boiling solvent to the dispersion and stirring to give a clear solution.

13. A process according to claim 12 wherein the inert cores of the beads are in the form of nonpareils.

14. A process according to claim 13 wherein the medicament is 1,2-dihydro-3-cyano-6-methyl-5-(4-pyridinyl)-2(1H)-pyridinone.

* * * * *

UNITED STATES PATENT AND TRADEMARK OFFICE
CERTIFICATE OF CORRECTION

PATENT NO. : 4,806,361
DATED     : February 21, 1989
INVENTOR(S) : Paul J. Harrison et al.

It is certified that error appears in the above-identified patent and that said Letters Patent is hereby corrected as shown below:

Column 5, line 25, "1 5," should read -- 1.5, --.

Signed and Sealed this

Twenty-fourth Day of August, 1993

Attest:

BRUCE LEHMAN

Attesting Officer     Commissioner of Patents and Trademarks